US011197969B2

(12) United States Patent
He et al.

(10) Patent No.: US 11,197,969 B2
(45) Date of Patent: Dec. 14, 2021

(54) MINIATURE AIR FILTRATION ASSEMBLY FOR A MEDICAL FIELD

(71) Applicant: EFK Consulting, INC, Encino, CA (US)

(72) Inventors: Kongyuan He, Encino, CA (US); Kanru Xu, Encino, CA (US)

( * ) Notice: Subject to any disclaimer, the term of this patent is extended or adjusted under 35 U.S.C. 154(b) by 0 days.

(21) Appl. No.: 17/001,450

(22) Filed: Aug. 24, 2020

(65) Prior Publication Data

US 2020/0376213 A1 Dec. 3, 2020

Related U.S. Application Data

(60) Provisional application No. 63/016,136, filed on Apr. 27, 2020.

(51) Int. Cl.

| | |
|---|---|
| ***A61M 16/00*** | (2006.01) |
| ***A61M 16/06*** | (2006.01) |
| ***A61M 16/10*** | (2006.01) |

(52) U.S. Cl.

CPC ........ *A61M 16/0009* (2014.02); *A61M 16/06* (2013.01); *A61M 16/105* (2013.01);

(Continued)

(58) Field of Classification Search

CPC ....... A61B 1/015; A61B 1/267; A61B 18/006; A61M 16/009; A61M 16/06; A61M 16/105; A61M 2202/0208; A61M 2205/8206; A61M 2205/7509; A61M 2205/7527; A61M 16/0808; A61M 2206/10; A61M 2205/7518; A61M 2205/8237; A61M 2205/583; A61M 2205/07; A61M 2202/206; A61M 16/0488; A61M 16/0093; B01D 46/0028; B01D 46/12; F04D 17/00–18

(Continued)

(56) References Cited

U.S. PATENT DOCUMENTS

2012/0285459 A1* 11/2012 Sata ........................ A61L 9/205 128/205.12

2014/0366890 A1* 12/2014 Tao .................... A61M 16/009 128/849

(Continued)

*Primary Examiner* — Elliot S Ruddie

(74) *Attorney, Agent, or Firm* — Barry Choobin; Patent 360

(57) ABSTRACT

The present invention is directed to an assembly and method of use thereof for reducing microbial load in an airway of a patient. The assembly includes a miniature vacuum unit. The miniature vacuum unit includes a housing, at least one air inlet configured in the housing for air intake; a vacuum motor for sucking the air through the at least one air inlet; vents configured in the housing for blowing the sucked air out of the housing, a filter media covering inner side of the vents, such as the sucked air passes through the filter media, the filter media configured to retain microbes suspended in the sucked air; and at least one suction tube. The suction tube is having a proximal end and a distal end, the proximal end of the at least one suction tube configured to sealably and releasably coupled to the at least one air inlet, a plurality of apertures configured in the wall of the suction tube near its distal end. The suction tube configured to be positioned within the mouth of the patient.

5 Claims, 14 Drawing Sheets

1440
1450
1420
1430
1410
1400

(52) U.S. Cl.
CPC ............... *A61M 2202/0208* (2013.01); *A61M 2205/7509* (2013.01); *A61M 2205/8206* (2013.01)

(58) Field of Classification Search
USPC ........................................ 128/205.12, 205.19
See application file for complete search history.

(56) References Cited

U.S. PATENT DOCUMENTS

| | | | | |
|---|---|---|---|---|
| 2017/0049606 | A1* | 2/2017 | Chen ................. | A61M 16/0057 |
| 2020/0069850 | A1* | 3/2020 | Beadle ................ | A61M 1/0088 |

* cited by examiner

MINIATURE AIR FILTRATION ASSEMBLY FOR A MEDICAL FIELD

CROSS-REFERENCE TO RELATED APPLICATIONS

This application claims priority to the U.S. provisional patent application Ser. No. 63/016,136 filed on Apr. 27, 2020, which is incorporated herein by reference in its entirety.

FIELD OF INVENTION

The present invention relates to an air filtration assembly and particularly relates to an air filtration assembly for filtering pathogens in an airway of a patient, such as during airway management.

BACKGROUND

Microbes that cause diseases in humans are known as pathogens. The most generic form of pathogens that cause diseases in humans include bacteria, virus, and fungi. Pathogens can transmit in many ways, for example, through the contaminated food, hands, air, sex, blood, and other bodily secretions, or the fecal-oral route. The microbes that can directly spread from person to person are known as contagious pathogens. The contagious pathogens can spread from an infected person to another person by physical contact or contact with secretions or objects touched by the infected person. Another common way of the spread of pathogenic microbes, particularly viruses, is the aerosol transmission or the droplets blown in the air by an infected person while breathing, coughing, or sneezing.

A medical staff taking care of an infected person are particularly at an elevated risk of getting infected. The COVID-19 outbreak in 2020 resulted in several morbidities and mortalities of healthcare workers because of acquiring the infection from the patients. The major challenges in managing patients with COVID-19 infection or other respiratory infections are bilateral pneumonia and acute respiratory distress syndrome. Despite using protective facemask and gloves, the chances of acquiring the infections are still higher. Generally, the patients are hospitalized when their health condition gets critical. Often, such patient, particularly those having an infected respiratory system, requires airway management, such as endotracheal intubation. Endotracheal intubation is a medical procedure wherein an endotracheal tube is passed through the patient's mouth and the vocal apparatus into the trachea. Commonly, during the intubation, the face of the operator is usually about one foot away from the patient's mouth. Typically, the viral and/or bacterial load in the patient's airway is probably extremely high and is contagious. Such proximity of the operator during endotracheal intubation or a similar medical procedure that involves mouth or airway can exponentially increase the risk of acquiring the infection. The anesthesiologists are at an elevated risk of becoming infected because of their close contact with patients. They are directly exposed to respiratory droplets or aerosol from the patients' airway. The healthcare workers whose job require them to have their faces in proximity to a patient's mouth are at an elevated risk of acquiring the injection.

The recent outbreak of Covid-19 showed that the safety of the health care workers and the magnitude of challenges in healthcare practice are far greater than anticipated. Most of the time these challenging situations are unavoidable. Thus, an urgent need is there for a solution to provide additional safety for health care workers. A need is appreciated for an assembly that can limit the spread of pathogens. A need is there for an assembly that can decrease the pathogen load near the mouth of an infected person.

The term bioaerosol hereinafter connotes microbes suspended in air and also includes the droplets blown in the air.

SUMMARY OF THE INVENTION

The principal object of the present invention is therefore directed to an assembly for reducing pathogen load near the mouth of an infected person.

It is another object of the present invention that the assembly can be used with known medical devices.

It is still another object of the present invention that the assembly can be used with a conventional laryngoscope.

It is yet another object of the present invention that the assembly decreases the chances of acquiring infection by the healthcare worker during a medical procedure.

It is yet another object of the present invention that the assembly decreases microbial load in an airway of a patient wearing an oxygen mass.

It is a further object of the present invention that the assembly is economical to manufacture and easy to use.

It is still a further object of the present invention that the assembly does not interfere with a medical procedure.

It is an additional object of the present invention that the assembly does not cause discomfort to the patient.

It is still an additional object of the present invention that the assembly can be single-use and disposable.

It is an object of the present invention that the assembly provides additional protection to the medical staff.

In one aspect, disclosed herein is an assembly for reducing microbial load in an airway of a patient while the patient is undergoing a medical procedure or wearing an oxygen mask. The assembly can also be used by an infected person wearing a protective facemask. The assembly includes a miniature vacuum unit. The miniature vacuum unit includes a housing, at least one air inlet configured in the housing for air intake; a vacuum motor for sucking the air through the at least one air inlet; vents configured in the housing for blowing the sucked air out of the housing, a filter media covering inner side of the vents, such as the sucked air passes through the filter media, the filter media configured to retain microbes suspended in the sucked air; and at least one suction tube. The suction tube having a proximal end and a distal end, the proximal end of the at least one suction tube configured to sealably and releasably coupled to the at least one air inlet, a plurality of apertures configured in a wall of the suction tube near its distal end.

In one aspect, the miniature vacuum unit is cubical of a dimension of 1 cubic inch. The miniature vacuum unit can further include a UV lamp enclosed in the housing and configured to irradiate the filter media.

In one aspect, the suction tube can further comprise a branch tube that branches from near middle portion of the at least one suction tube, the lumen of the branch tube is in fluid communication with the lumen of the suction tube, the branch tube having apertures configured in the wall of the branch tube.

In one aspect, the assembly includes a laryngoscope, the laryngoscope having a handle and a spatula, the miniature vacuum unit releasably coupled to the handle, the branch tube fastened to the spatula.

In one aspect, the assembly includes two air inlets, a first air inlet, and a second air inlet, and two suction tubes. The first suction tube at its proximal end can couple to the first air inlet, and a second suction tube at its proximal end can couple to the second air inlet. The second suction tube can fasten to the spatula. In one aspect, the assembly includes an oxygen mask, the distal end of the first suction tube inserted into the oxygen mask, the second suction tube wrap around the oxygen mask.

In one aspect, the suction tube can include an inner lining of absorbent material, the inner lining positioned near the proximal end of the at least one suction tube. The suction tube may also include a drain port, the drain port positioned near the proximal end of the suction tube.

In one aspect, disclosed is a method for reducing microbial load in an airway of a patient during a medical procedure. The method is the method of using the above assembly for reducing microbial load by positioning the suction tube within the mouth of the patient and sucking air through the apertures of the first secondary tube. The second suction tube can be positioned outside the mouth and the air can be sucked from both the suction tubes.

These and other objects and advantages of the embodiments herein will become readily apparent from the following detailed description.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
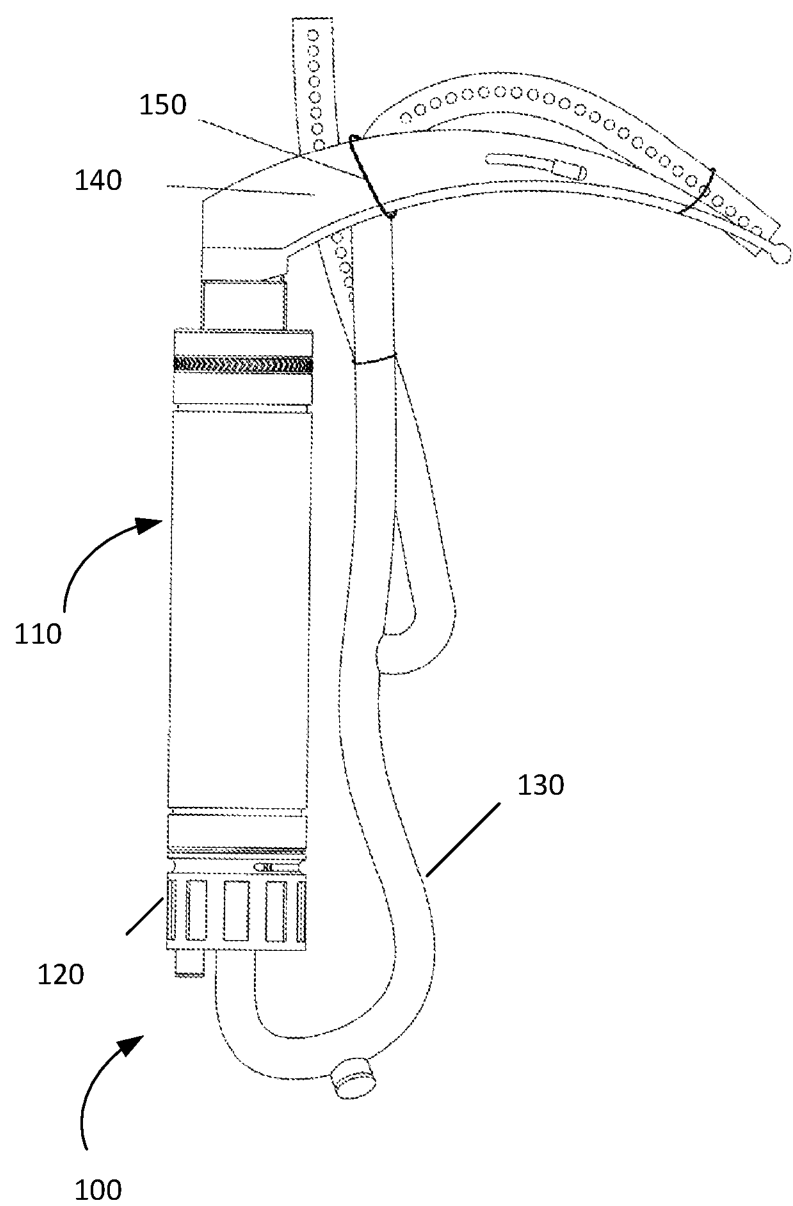
FIG. 1 shows an assembly coupled to a laryngoscope, according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as assembly and methods of use thereof. The following detailed description is, therefore, not intended to be taken in a limiting sense.

The word “exemplary” is used herein to mean “serving as an example, instance, or illustration.” Any embodiment described herein as “exemplary” is not necessarily to be construed as preferred or advantageous over other embodiments. Likewise, the term “embodiments of the present invention” does not require that all embodiments of the invention include the discussed feature, advantage, or mode of operation.

The terminology used herein is for the purpose of describing particular embodiments only and is not intended to be limiting of embodiments of the invention. As used herein, the singular forms “a”, “an” and “the” are intended to include the plural forms as well, unless the context clearly indicates otherwise. It will be further understood that the terms “comprises”, “comprising,”, “includes” and/or “including”, when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth to provide a thorough understanding of the subject innovation. It may be evident, however, that the claimed subject matter may be practiced without these specific details.

The present disclosure is directed to an assembly for reducing bioaerosol load near the mouth of a patient. The assembly disclosed herein includes a miniature vacuum unit and a suction tubing. Referring to FIG. 1, which shows the assembly 100 coupled to a bottom of a conventional laryngoscope 110. The assembly 100 includes the miniature vacuum unit 120 and the suction tubing 130. The tubing 130 can be seen coupled to an air inlet of the miniature vacuum unit 120. The laryngoscope 110 is having a spatula 140 to which the suction tubing 130 is hooked using a hook line 150. It is to be understood that the assembly disclosed herein is illustrated with the aid of a laryngoscope, however, the assembly can be used alone or with any other medical device.

Figure 2:
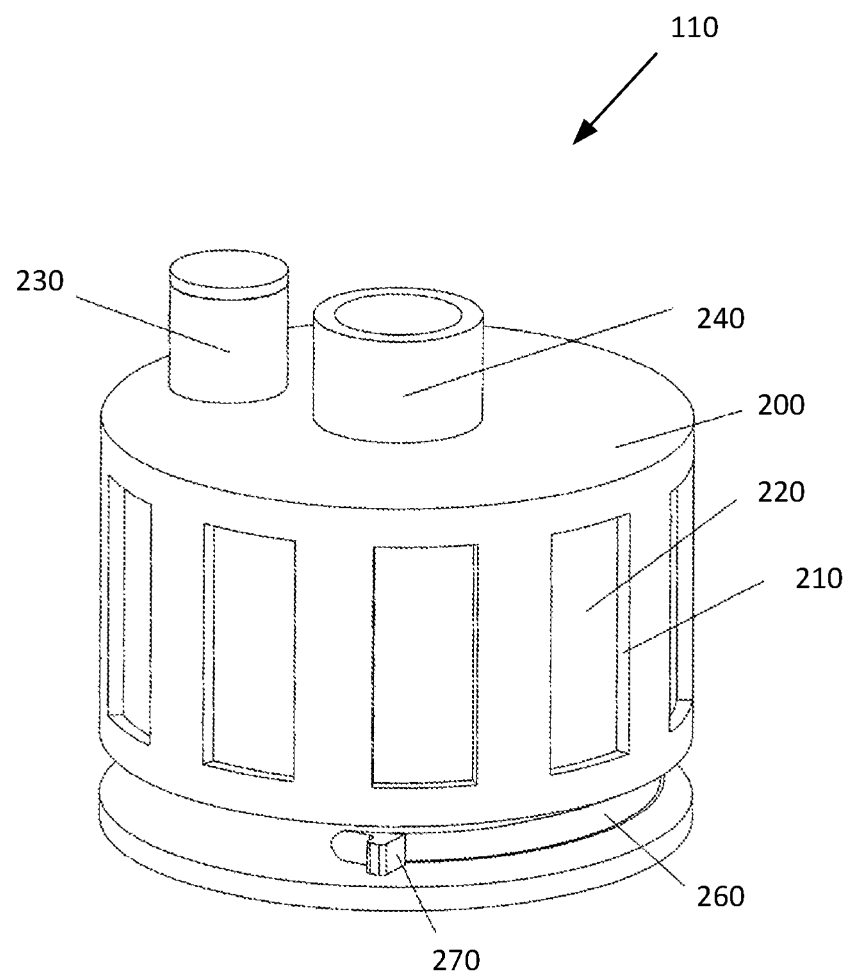
FIG. 2 is a perspective view of a miniature vacuum unit, according to an exemplary embodiment of the present invention.

Referring to FIG. 2 which shows a perspective view of the miniature vacuum unit 120. The miniature vacuum unit 120 can suck air and filter the microbes suspended in the sucked air. Through the suction tubing 130, the miniature vacuum unit 120 can suck air from the patient's mount and the environment in immediate proximity to the patient's mouth. The miniature vacuum unit 120 can retain bioaerosols blown in the air while the patient breathes. The air blown from the patient's airway including the droplets can be sucked and filtered by the miniature vacuum unit 120. The miniature vacuum unit 120 is small and light in weight, thus can be easily positioned near the mouth of the patient. The miniature vacuum unit 120 can include a housing 200, the housing having multiple vents 210 for the air to pass through, a miniature vacuum motor (not shown) that can suck air, and a filter media 220 covering the multiple vents 210 of the housing 200 from its inner side. The air sucked by the vacuum motor passes through the filter medium, wherein bioaerosols are retained on the filter medium. The miniature vacuum unit 120 is shown to be having two air inlets, the first air inlet 230 and a second air inlet 240. Through the air inlets, the vacuum motor can suck the air. Also, the air inlets can provide for attaching the suction tube to the miniature vacuum unit. The air inlets can be capped, such that either one of the air inlets can be used. Both air inlets can also be used. For example, one of the air inlets can be coupled to the tubing while the other inlet is open to suck air from its immediate environment. It is to be noted that although FIG. 2 shows two air inlets, the miniature vacuum unit can have one, three or more air inlets.

Also, it is to be noted that although Figures show the miniature vacuum unit as cylindrical, however, it can be manufactured in different shapes including cube, cuboidal, and like. In one case, the size of the miniature vacuum unit is small having length and width of about 1 inch. In one case, the miniature vacuum unit is cubic having a dimension of about 1 cubic inch.

Figure 3:
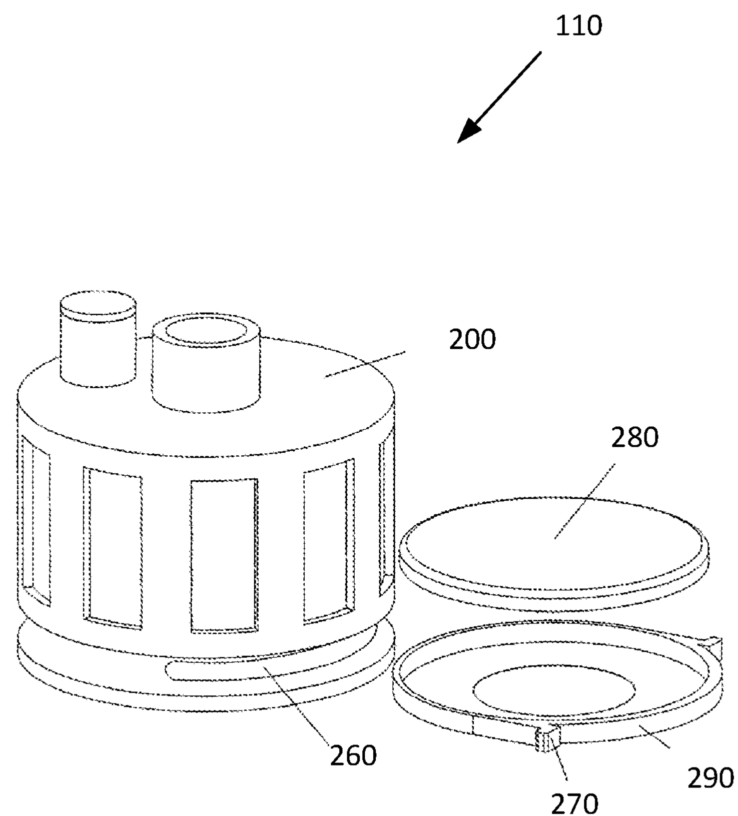
FIG. 3 is a perspective view of the miniature vacuum unit of FIG. 2 having a battery cover removed and showing the battery, according to an exemplary embodiment of the present invention.
Figure 4:
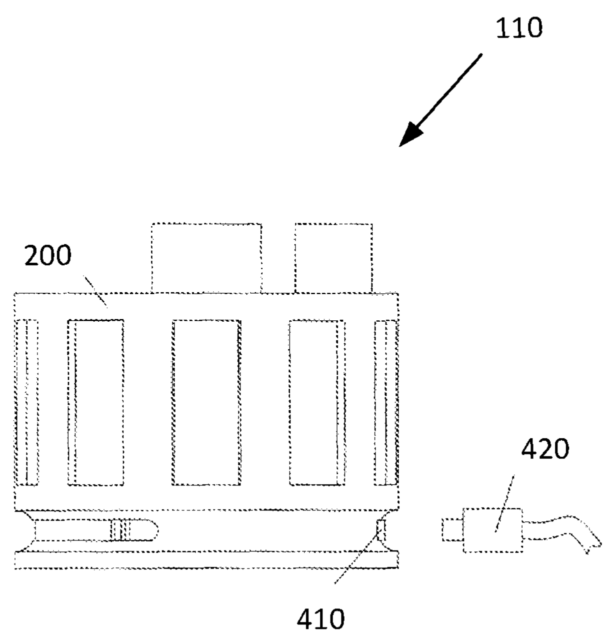
FIG. 4 shows the miniature vacuum unit and a charging cable, according to an exemplary embodiment of the present invention.

The miniature vacuum unit can be powered by a battery. The battery can be housed in a battery compartment 260 shown at the bottom of the miniature vacuum unit 120. The battery compartment 260 can be locked and unlocked using a slide button 270. FIG. 3 shows the battery 280 and the battery cover 290 removed from the housing 200. The battery 280 shown in FIG. 3 is a button-shaped battery. The bottom of the miniature vacuum unit 120 can be configured with a battery compartment that can house one or more miniature size battery, such as the button-shaped battery shown in FIG. 3. The number of batteries can be based on the desired voltage. The battery compartment is closed by a removable battery cover. The battery can be a rechargeable or non-rechargeable battery. For example, lithium-ion rechargeable batteries are known. Additionally, the miniature vacuum unit can also be powered by an external direct current. FIG. 4 shows the miniature vacuum unit 120 having a charging port near the bottom portion of the housing 200. This charging port 410 can receive a power cable 420 carrying a direct current from a DC power source. In one case, the external DC power source can be an electrical supply of the laryngoscope. Additionally, the rechargeable batteries can be charged using the charging port. Alternatively, the external direct current can be used to charge the battery, while the miniature vacuum unit draws current from the battery. The miniature vacuum unit can be configured to simultaneously charge the battery and use the current from the battery to run the vacuum motor.

Figure 5:
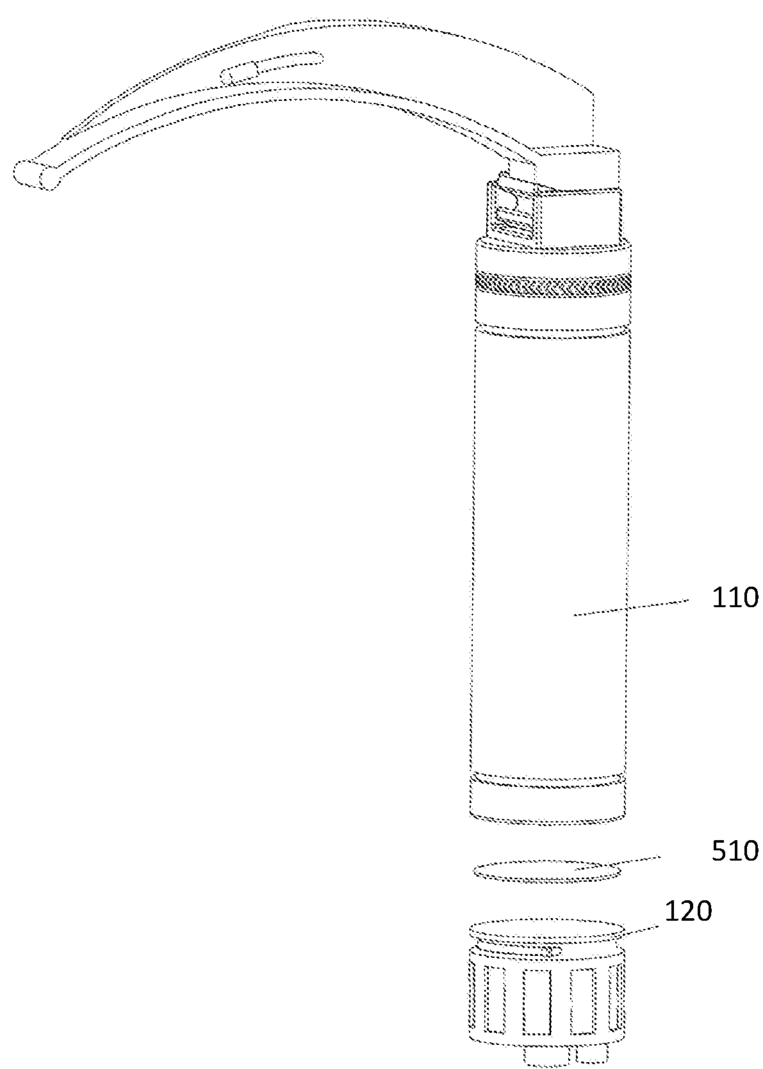
FIG. 5 shows the miniature vacuum unit, an adhesive pad, and the laryngoscope, according to an exemplary embodiment of the present invention.
Figure 6:
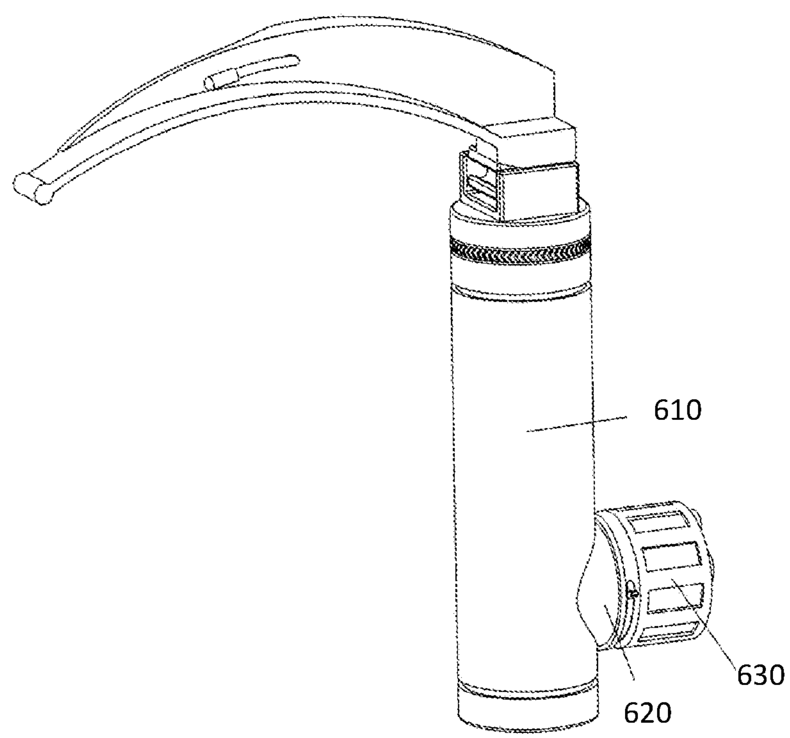
FIG. 6 shows the miniature vacuum unit attached to side of the laryngoscope, according to an exemplary embodiment of the present invention.
Figure 7:
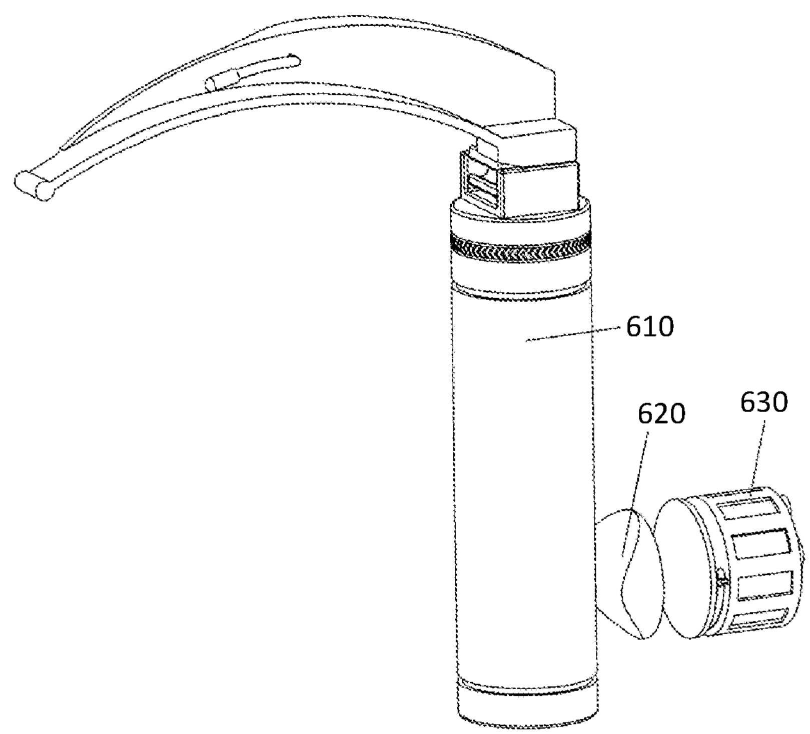
FIG. 7 shows the miniature vacuum unit, a curved adhesive pad, and the laryngoscope, according to an exemplary embodiment of the present invention.

FIG. 5 shows the miniature vacuum unit 120, a double-sided adhesive pad 510, and a laryngoscope 110. The miniature vacuum unit 120 can be connected to the bottom of the laryngoscope 110 using the double-sided adhesive pad 510. Thus, the miniature vacuum unit 120 can be easily attached and removed from any conventional laryngoscope. Moreover, the miniature vacuum unit 120 can be easily attached to any other medical device. FIG. 5 shows the miniature vacuum unit 120 attached to the bottom of the laryngoscope, however, the miniature vacuum unit 120 can also be attached to the wall of the laryngoscope. FIG. 6 shows the miniature vacuum unit 630 attached to the handle of the laryngoscope 610 through an adhesive pad 620. FIG. 7 shows the miniature vacuum unit 630 and the adhesive pad 620 separated from the laryngoscope 610. The adhesive pad is double-sided and curved to conform to the shape of the laryngoscope.

Figure 8:
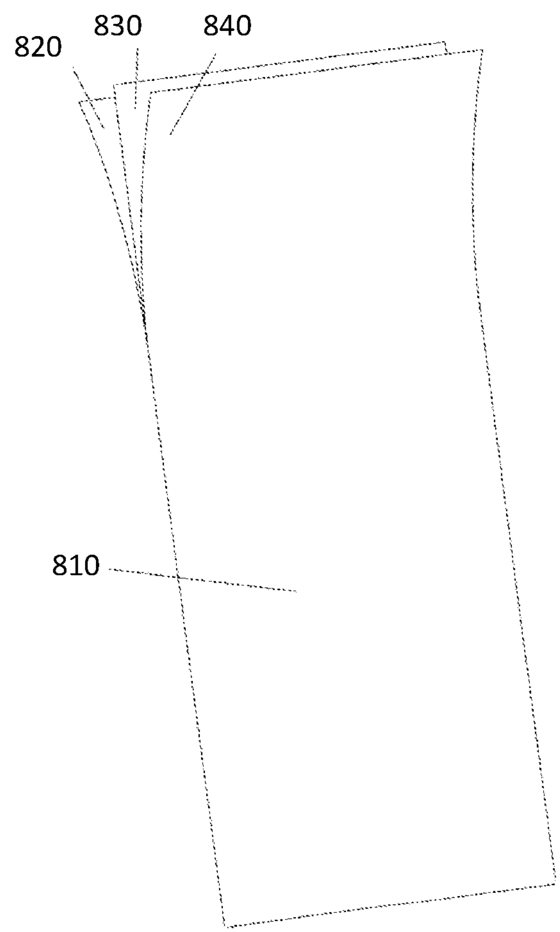
FIG. 8 shows an exemplary embodiment of a three-layer filter media for microbes, according to an exemplary embodiment of the present invention.

The miniature vacuum unit disclosed herein sucks air from the patient's mouth and nearby the mouth and filters the air using a filter media. The filter media can have a pore size that can retain microbes including the viruses. The filter media can be supported against the vents of the housing and the sucked by the vacuum motor can pass through the filter media and blown outside through the vents. FIG. 8 shows one exemplary embodiment of the filter media 800 having three layers, the first layer 810, the second layer 820, and the third layer 830. The first layer can have a pore size different from the second layer, and the second layer can have a pore size different from the third layer. Besides using the filter media, a UV lamp can also be included in the housing, such as the filter media is exposed to UV radiation. The UV radiation can sterilize the filter media, thus reducing the microbial load on the filter media. This improves the efficiency and life of the filter media, as well as improving the air filtration.

Figure 9:
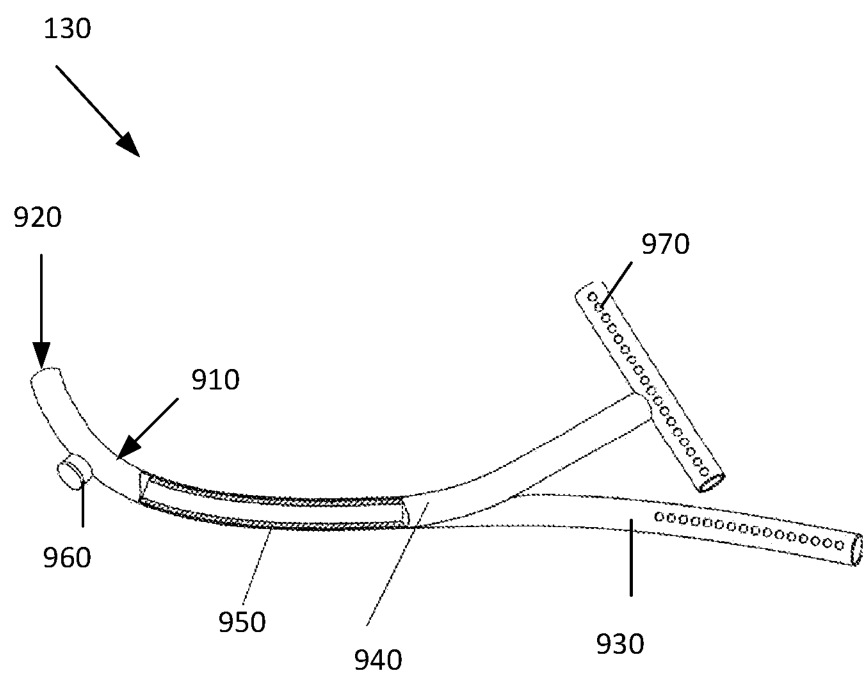
FIG. 9 shows a suction tube, according to an exemplary embodiment of the present invention.
Figure 10:
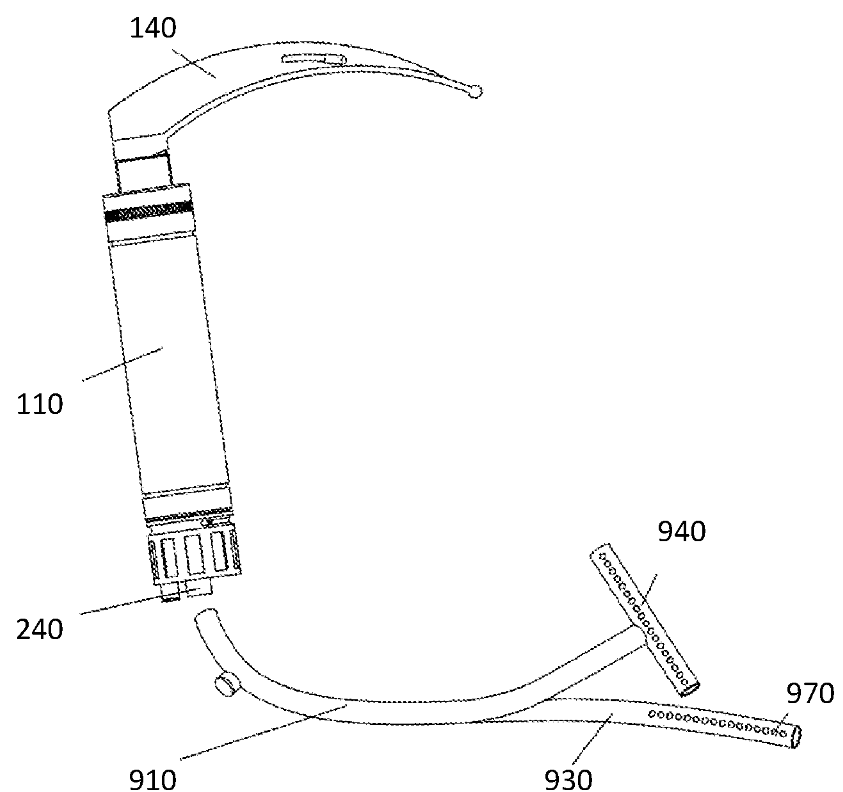
FIG. 10 shows a miniature vacuum unit and the suction tube, according to an exemplary embodiment of the present invention.

FIG. 9 shows an embodiment of the suction tube 130 having a primary tube 910. The primary tube can have a proximal end 920 and a distal end. The proximal end of the primary tube can be connected to the air inlet of the miniature vacuum unit. FIG. 1 shows the proximal end of the primary tube attached to the air inlet of the miniature vacuum unit. To further clarify the attachment, the primary tube is also shown separated from the air inlet in FIG. 10. The air inlet and the proximal end of the primary tube can be structured to sealably couple with each other. For example, the proximal end of the suction tube can frictionally grip around the air inlet. Such a structure for attaching a tube to a nozzle is known in the art. Referring again to FIG. 9, the suction tube at the distal end of the primary tube is shown to be bifurcated into two secondary tubes. It is to be noted that the suction tube can be a single prolonged primary tube. Alternatively, more than two branches of secondary tubes can extend from the primary tube. Perhaps, FIG. 9 shows the primary tube is extended to form the secondary tube 930, while the secondary tube 940 branches from the continuous primary tube 910 and the secondary tube 930.

One of the two secondary tubes shown in FIG. 9, referred herein as the first secondary tube 930 and the second secondary tube 940, the first secondary tube 930 is straight. While the second secondary tube is of T-shape. Both the secondary tubes are shown to have a plurality of apertures for drawing air into the secondary tubes. The sucked air from the secondary tubes is drawn into the common primary tube by the miniature vacuum unit. As shown in FIG. 1, the first secondary tube is attached to the spatula of the laryngoscope. While the T-shaped secondary tube can be positioned outside the mouth for drawing air from the proximity of the mouth. However, it is to be understood that the T-shape provides more surface area, but the shape of both of the secondary tubes can be varied without departing from the scope of the present invention.

Figure 11:
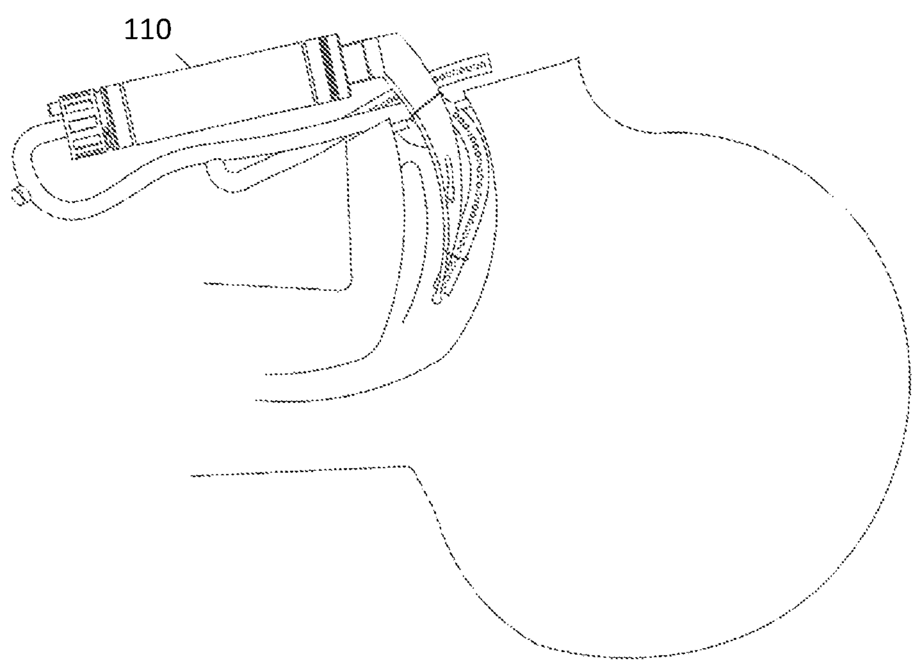
FIG. 11 shows the assembly positioned in a mouth of a patient, according to an exemplary embodiment of the present invention.
Figure 12:
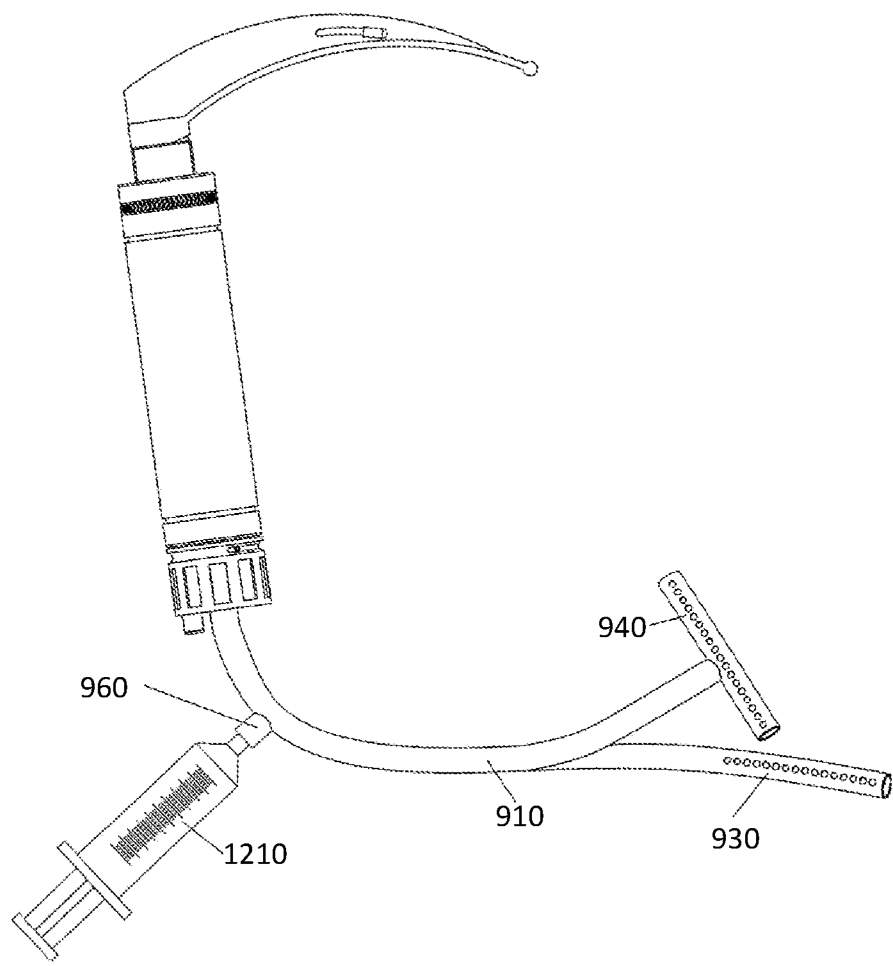
FIG. 12 shows a syringe coupled to a drainage port of the suction tube, according to an exemplary embodiment of the present invention.

FIG. 11 shows the assembly coupled to a laryngoscope, as shown in FIG. 1, and inserted into an airway of a patient. One of the secondary tubes is within the mouth, while the other secondary tube is above the opening of the mouth. The secondary tube inside the mouth is fastened to the spatula of the laryngoscope through a hook line. The other empty air inlet of the miniature vacuum unit can be capped. To use the assembly, disclosed herein, It is advisable to aspirate any fluids from the mouth of the patient before inserting the suction tube. However, due to the vacuum, fluids from the mouth can be aspirated into the suction tube. Because of the aspirated fluids, the suction tubes can be made transparent such as any fluid is visible inside the tube. The fluid can collect in the tube itself. Alternatively, an appendage, such as a short tube can also extend from the suction tube and in fluid communication with the lumen of the suction tube. The fluid can flow into the appendage and collect. A portion of the suction tube can also be provided with an inner lining of an absorbent material that can retain the fluid and prevent the fluid from reaching the miniature vacuum unit. FIG. 9 shows an inner lining 950 in the primary tube. The inner line can additionally provide a drag the flow of the fluid inside the primary tube, such that the fluid, under vacuum, cannot rush into the miniature vacuum unit and damage it. Adjacent the inner lining 950 and near the proximal end is a drainage port 960 for collecting fluid. FIG. 12 shows a syringe 1210 coupled to the drainage port 960 for drawing the fluid from the suction tube.

Figure 13:
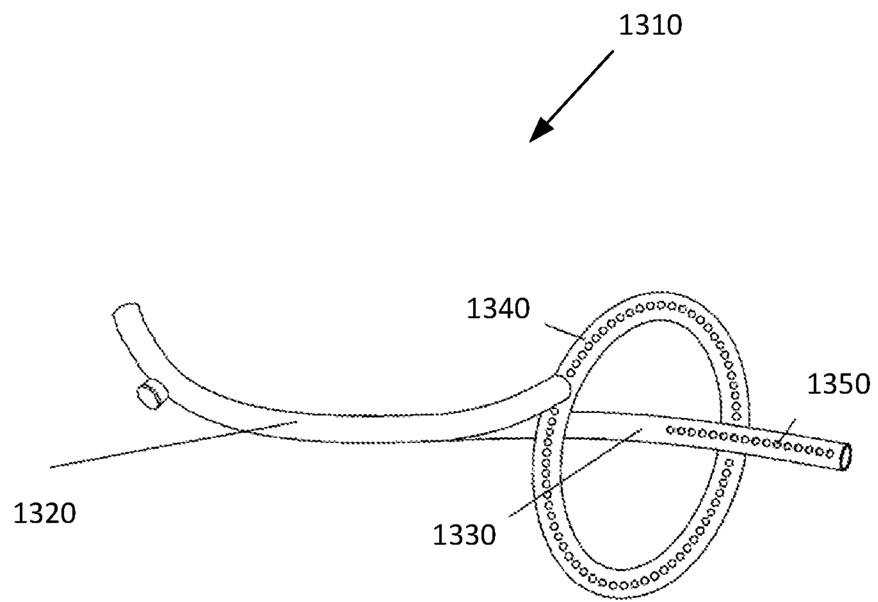
FIG. 13 shows a suction tube for an oxygen mask, according to an exemplary embodiment of the present invention.

In one embodiment, the assembly disclosed herein can also be used with an oxygen mask. In case, the patient is wearing an oxygen mask, the assembly disclosed herein can decrease the bioaerosol load in and around the oxygen mask. FIG. 13 shows an embodiment of the suction tube 1310 adapted for the oxygen mask. FIG. 13 shows the suction tube 1310 having a primary tube 1320, a first secondary tube 1350 continuous with the primary tube 1320. A second secondary tube 1340 branches out from the primary tube. The second secondary tube 1340 is circular that can wrap around the oxygen mask. Both the secondary tubes are having apertures 1350 for drawing the air.

Figure 14:
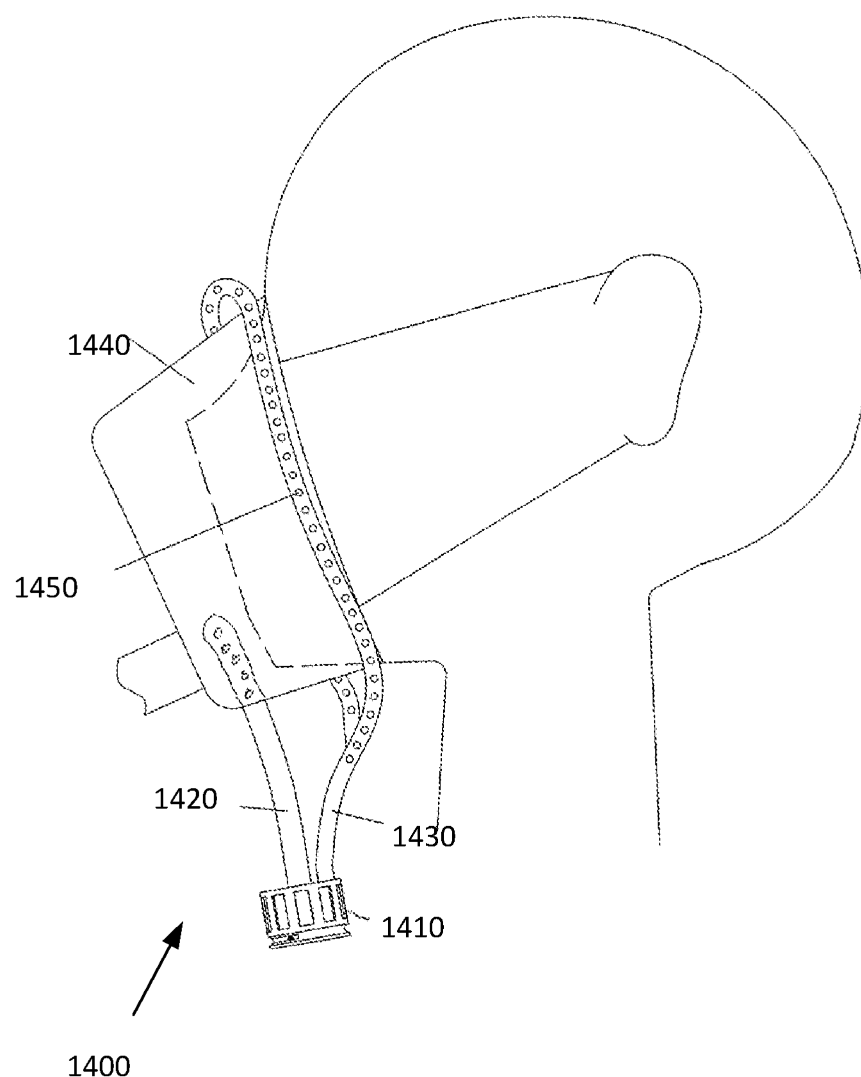
FIG. 14 shows the oxygen mask with the suction tube, according to an exemplary embodiment of the present invention.

FIG. 14 shows another embodiment of the assembly 1400. The assembly 1400 includes a miniature vacuum unit 1410 as disclosed herein. The miniature vacuum unit 1410 is having two air inlets to which two suction tubes are shown to be attached. One short suction tube 1420 extends into the oxygen mask 1440. The other suction tube 1430 wraps around the oxygen mask 1440.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A method for reducing microbial load in an airway of a patient wearing an oxygen mask, the method comprising:

providing an assembly, the assembly comprising:
- a miniature vacuum unit configured to suck air under pressure, the miniature vacuum unit comprises:
  - a cylindrical housing, the cylindrical housing having a top, a base, a wall that extends between a periphery of the top and the base, a plurality of elongated vents arranged side-by-side in the wall,
  - a filter media configured to cover the plurality of elongated vents to retain microbes suspended in the sucked air, and
  - a first air inlet and a second air inlet in the top of the cylindrical housing,
- a first suction tube having a proximal end and a distal end, the proximal end coupled to the first air inlet, the first suction tube having apertures configured near the distal end, and
- a second suction tube coupled to the second air inlet, the second suction tube having apertures;

positioning the first suction tube within the oxygen mask worn by the patient, wherein the apertures of the first suction tube are within the oxygen mask;

positioning the second suction tube around the oxygen mask; and sucking air through the apertures of the first suction tube and the second suction tube.

2. An assembly for reducing microbial load in an airway of a patient, the assembly comprising:
- a miniature vacuum unit, the miniature vacuum unit comprising:
  - a housing, the housing having a top, a base, a wall that extends between a periphery of the top and the base;
  - a plurality of elongated vents arranged side-by-side in the wall;
  - a first air inlet, a second air inlet, wherein the first air inlet and second air inlet are configured in the top of the housing for air intake;
  - a vacuum motor enclosed in the housing for sucking the air through the first air inlet and the second air inlet;
  - a filter media covering an inner side of the plurality of elongated vents configured such that the sucked air passes through the filter media, the filter media configured to retain microbes suspended in the sucked air;
  - a first suction tube having a proximal end and a distal end, the proximal end of the first suction tube configured to sealable and releasable couple to the first air inlet;
  - a second suction tube having a proximal end and a distal end, the proximal end of the second suction tube configured to sealable and releasable couple to the second air inlet; and
  - wherein the first suction tube having apertures configured near the distal end, and the second suction tube having apertures.

3. The assembly of claim 2, wherein the miniature vacuum unit is cubical in shape and having a volume of about 1 cubic inch.

4. The assembly of claim 3, wherein the miniature vacuum unit further comprises a UV lamp enclosed in the housing, the UV lamp configured to irradiate the filter media.

5. The assembly of claim 2, further comprise an oxygen mask; wherein the distal end of the first suction tube is configured to be inserted into the oxygen mask and the second suction tube is configured to wrap around the oxygen mask.

* * * * *